United States Patent
Shelton

(10) Patent No.: US 10,905,884 B2
(45) Date of Patent: Feb. 2, 2021

(54) MULTI-STAGE ATRIAL CARDIOVERSION THERAPY LEADS

(71) Applicant: CardiaLen, Inc., St. Louis, MO (US)

(72) Inventor: Michael Brent Shelton, Golden Valley, MN (US)

(73) Assignee: Cardialen, Inc., Minneapolis, MN (US)

( * ) Notice: Subject to any disclaimer, the term of this patent is extended or adjusted under 35 U.S.C. 154(b) by 1414 days.

(21) Appl. No.: 13/947,840

(22) Filed: Jul. 22, 2013

(65) Prior Publication Data

US 2014/0058470 A1    Feb. 27, 2014

Related U.S. Application Data

(60) Provisional application No. 61/674,145, filed on Jul. 20, 2012.

(51) Int. Cl.
*A61N 1/36* (2006.01)
*A61N 1/365* (2006.01)
*A61N 1/368* (2006.01)
*A61N 1/362* (2006.01)

(52) U.S. Cl.
CPC ....... *A61N 1/36514* (2013.01); *A61N 1/3624* (2013.01); *A61N 1/3686* (2013.01)

(58) Field of Classification Search
CPC .... A61N 1/395; A61N 1/3624; A61N 1/3962; A61N 1/3622
USPC .......................................................... 607/17
See application file for complete search history.

(56) References Cited

U.S. PATENT DOCUMENTS

| | | | |
|---|---|---|---|
| 3,729,008 | A | 4/1973 | Berkovits |
| 3,738,370 | A | 6/1973 | Charms |
| 3,942,536 | A | 3/1976 | Mirowski et al. |
| 4,136,703 | A | 1/1979 | Wittkampf |
| 4,312,356 | A | 1/1982 | Sowton et al. |
| 4,384,585 | A | 5/1983 | Zipes |
| 4,390,021 | A | 6/1983 | Spurrell et al. |

(Continued)

FOREIGN PATENT DOCUMENTS

| | | |
|---|---|---|
| EP | 0 393 265 A1 | 10/1990 |
| EP | 1 062 971 A1 | 12/2000 |

(Continued)

OTHER PUBLICATIONS

Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996, USA.

(Continued)

*Primary Examiner* — Michael J D Abreu
(74) *Attorney, Agent, or Firm* — Bookoff McAndrews, PLLC

(57) ABSTRACT

Devices and methods of use for treating atrial arrhythmias. A single-pass lead includes a body portion having at least two electrodes configured to be positioned within or adjacent a right atrium of a heart of a patient, and a distal portion having at least two electrodes configured to be positioned within a blood vessel proximate the left atrium. The lead is configured to operated by an implantable therapy generator programmed to deliver a multi-stage therapy by activating various combinations of at least one electrode of the body portion of the lead and at least one electrode of the distal portion of the lead.

20 Claims, 4 Drawing Sheets

(56) References Cited

U.S. PATENT DOCUMENTS

| | | |
|---|---|---|
| 4,398,536 A | 8/1983 | Nappholz et al. |
| 4,403,614 A | 9/1983 | Engle et al. |
| 4,408,606 A | 10/1983 | Spurrell et al. |
| 4,488,554 A | 12/1984 | Nappholz et al. |
| 4,727,877 A | 3/1988 | Kallok |
| 4,768,512 A | 9/1988 | Imran |
| 4,799,493 A | 1/1989 | DuFault |
| 4,932,407 A | 6/1990 | Williams |
| 4,996,984 A | 3/1991 | Sweeney |
| 4,998,975 A | 3/1991 | Cohen et al. |
| 5,007,436 A | 4/1991 | Smits |
| 5,014,696 A | 5/1991 | Mehra |
| 5,099,838 A | 3/1992 | Bardy |
| 5,107,834 A | 4/1992 | Ideker et al. |
| 5,111,811 A | 5/1992 | Smits |
| 5,144,960 A | 9/1992 | Mehra et al. |
| 5,163,427 A | 11/1992 | Keimel |
| 5,170,802 A | 12/1992 | Mehra |
| 5,174,288 A | 12/1992 | Bardy et al. |
| 5,184,616 A | 2/1993 | Weiss |
| 5,199,429 A | 4/1993 | Kroll et al. |
| 5,235,977 A | 8/1993 | Hirschberg et al. |
| 5,235,978 A | 8/1993 | Hirschberg et al. |
| 5,243,978 A | 9/1993 | Duffin, Jr. |
| 5,243,980 A | 9/1993 | Mehra |
| 5,247,929 A | 9/1993 | Stoop et al. |
| 5,261,400 A | 11/1993 | Bardy |
| 5,265,600 A | 11/1993 | Adams et al. |
| 5,269,319 A | 12/1993 | Schulte et al. |
| 5,275,621 A | 1/1994 | Mehra |
| 5,279,291 A | 1/1994 | Adams et al. |
| 5,282,836 A | 2/1994 | Kreyenhagen et al. |
| 5,292,338 A | 3/1994 | Bardy |
| 5,292,339 A | 3/1994 | Stephens et al. |
| 5,306,291 A | 4/1994 | Kroll et al. |
| 5,314,430 A | 5/1994 | Bardy |
| 5,324,309 A | 6/1994 | Kallok |
| 5,330,509 A | 7/1994 | Kroll et al. |
| 5,334,219 A | 8/1994 | Kroll |
| 5,344,429 A | 9/1994 | Smits |
| 5,350,403 A | 9/1994 | Stroetmann et al. |
| 5,360,435 A | 11/1994 | DeGroot |
| 5,365,391 A | 11/1994 | Sugiyama et al. |
| 5,366,484 A | 11/1994 | Kroll |
| 5,372,605 A | 12/1994 | Adams et al. |
| 5,374,279 A | 12/1994 | Duffin, Jr. et al. |
| 5,374,287 A | 12/1994 | Rubin |
| 5,376,103 A | 12/1994 | Anderson et al. |
| 5,383,907 A | 1/1995 | Kroll |
| 5,383,908 A | 1/1995 | Sweeney et al. |
| 5,385,575 A | 1/1995 | Adams |
| 5,387,613 A | 2/1995 | Goldberg et al. |
| 5,391,185 A | 2/1995 | Kroll |
| 5,391,186 A | 2/1995 | Kroll et al. |
| 5,403,351 A | 4/1995 | Saksena |
| 5,403,356 A | 4/1995 | Hill et al. |
| 5,405,363 A | 4/1995 | Kroll et al. |
| 5,405,374 A | 4/1995 | Stein |
| 5,407,444 A | 4/1995 | Kroll |
| 5,413,591 A | 5/1995 | Knoll |
| 5,423,865 A | 6/1995 | Bowald et al. |
| 5,431,683 A | 7/1995 | Bowald et al. |
| 5,433,729 A | 7/1995 | Adams et al. |
| 5,439,481 A | 8/1995 | Adams |
| 5,439,484 A | 8/1995 | Mehra |
| 5,441,518 A | 8/1995 | Adams et al. |
| 5,449,377 A | 9/1995 | Adams et al. |
| 5,476,502 A | 12/1995 | Rubin |
| 5,489,293 A | 2/1996 | Pless et al. |
| 5,514,160 A | 5/1996 | Kroll et al. |
| 5,522,853 A | 6/1996 | Kroll |
| 5,531,764 A | 7/1996 | Adams et al. |
| 5,534,019 A | 7/1996 | Paspa |
| 5,545,181 A | 8/1996 | Jacobson et al. |
| 5,545,182 A | 8/1996 | Stotts et al. |
| 5,545,186 A | 8/1996 | Olson et al. |
| 5,545,189 A | 8/1996 | Fayram |
| 5,545,204 A | 8/1996 | Cammilli et al. |
| 5,545,205 A | 8/1996 | Schulte et al. |
| 5,549,642 A | 8/1996 | Min et al. |
| 5,562,708 A | 10/1996 | Combs et al. |
| 5,591,211 A | 1/1997 | Meltzer |
| 5,601,607 A | 2/1997 | Adams |
| 5,620,464 A | 4/1997 | Kroll et al. |
| 5,620,468 A | 4/1997 | Mongeon et al. |
| 5,620,469 A | 4/1997 | Kroll |
| 5,620,477 A | 4/1997 | Pless et al. |
| 5,626,619 A | 5/1997 | Jacobson et al. |
| 5,628,778 A | 5/1997 | Kruse et al. |
| 5,630,834 A | 5/1997 | Bardy |
| 5,641,326 A | 6/1997 | Adams |
| 5,658,321 A | 8/1997 | Fayram et al. |
| 5,662,689 A | 9/1997 | Elsberry et al. |
| 5,662,692 A | 9/1997 | Paspa et al. |
| 5,674,248 A | 10/1997 | Kroll et al. |
| 5,676,687 A | 10/1997 | Ayers |
| 5,683,429 A | 11/1997 | Mehra |
| 5,683,431 A | 11/1997 | Wang |
| 5,690,686 A | 11/1997 | Min et al. |
| 5,713,924 A * | 2/1998 | Min ................. A61N 1/3962 607/4 |
| 5,713,926 A | 2/1998 | Hauser et al. |
| 5,718,718 A | 2/1998 | Kroll et al. |
| 5,722,995 A | 3/1998 | Olson et al. |
| 5,735,876 A | 4/1998 | Kroll et al. |
| 5,735,878 A | 4/1998 | Kroll et al. |
| 5,755,736 A | 5/1998 | Gillberg et al. |
| 5,755,742 A | 5/1998 | Scheulke et al. |
| 5,766,226 A | 6/1998 | Pedersen |
| 5,776,168 A | 7/1998 | Gunderson |
| 5,782,876 A | 7/1998 | Flammang |
| 5,792,187 A | 8/1998 | Adams |
| 5,797,967 A | 8/1998 | KenKnight |
| 5,813,999 A | 9/1998 | Ayers et al. |
| 5,814,079 A | 9/1998 | Kieval |
| 5,817,131 A | 10/1998 | Elsberry et al. |
| 5,830,236 A | 11/1998 | Mouchawar et al. |
| 5,836,975 A | 11/1998 | DeGroot |
| 5,840,079 A | 11/1998 | Warman et al. |
| 5,855,593 A | 1/1999 | Olson et al. |
| 5,871,510 A | 2/1999 | Kroll et al. |
| 5,891,043 A | 4/1999 | Ericksen et al. |
| 5,906,633 A | 5/1999 | Mouchawar et al. |
| 5,913,887 A | 6/1999 | Michel |
| 5,916,238 A | 6/1999 | Hauser et al. |
| 5,916,243 A | 6/1999 | KenKnight et al. |
| 5,925,066 A | 7/1999 | Kroll et al. |
| 5,928,270 A | 7/1999 | Ramsey, III |
| 5,928,271 A | 7/1999 | Hess et al. |
| 5,935,160 A | 8/1999 | Auricchio et al. |
| 5,987,356 A | 11/1999 | DeGroot |
| 5,995,871 A | 11/1999 | Knisley |
| 5,995,876 A | 11/1999 | Kruse et al. |
| 6,006,139 A | 12/1999 | Kruse et al. |
| 6,007,493 A | 12/1999 | Ericksen et al. |
| 6,026,332 A | 2/2000 | Kenknight et al. |
| 6,032,079 A | 2/2000 | KenKnight et al. |
| 6,038,483 A | 3/2000 | KenKnight et al. |
| 6,041,256 A | 3/2000 | Michel |
| 6,058,327 A | 5/2000 | Borgerding et al. |
| 6,059,739 A | 5/2000 | Baumann |
| 6,070,081 A | 5/2000 | Takahashi et al. |
| 6,081,745 A | 6/2000 | Mehra |
| 6,081,746 A | 6/2000 | Pendekanti et al. |
| 6,085,116 A | 7/2000 | Pendekanti et al. |
| 6,085,119 A | 7/2000 | Scheiner et al. |
| 6,091,988 A | 7/2000 | Warman et al. |
| 6,091,989 A | 7/2000 | Swerdlow et al. |
| 6,091,991 A | 7/2000 | Warren |
| 6,094,596 A | 7/2000 | Morgan |
| 6,096,064 A | 8/2000 | Routh |
| 6,134,470 A | 8/2000 | Routh |
| 6,146,338 A | 11/2000 | Gardeski et al. |
| 6,152,954 A | 11/2000 | Scheiner et al. |

(56) References Cited

U.S. PATENT DOCUMENTS

| | | | |
|---|---|---|---|
| 6,152,955 | A | 11/2000 | KenKnight et al. |
| 6,157,859 | A | 12/2000 | Alt |
| 6,157,860 | A | 12/2000 | Hauser et al. |
| 6,178,350 | B1 | 1/2001 | Olson et al. |
| 6,178,351 | B1 | 1/2001 | Mower |
| 6,185,459 | B1 | 2/2001 | Mehra et al. |
| 6,205,357 | B1 | 3/2001 | Ideker et al. |
| 6,212,434 | B1 | 4/2001 | Scheiner et al. |
| 6,233,483 | B1 | 5/2001 | Causey, III et al. |
| 6,246,906 | B1 | 6/2001 | Hsu et al. |
| 6,249,701 | B1 | 6/2001 | Rajasekhar et al. |
| 6,272,380 | B1 | 8/2001 | Warman et al. |
| 6,280,462 | B1 | 8/2001 | Hauser et al. |
| 6,292,691 | B1 | 9/2001 | Pendekanti et al. |
| 6,295,475 | B1 * | 9/2001 | Morgan ............ A61N 1/056 607/122 |
| 6,321,122 | B1 | 11/2001 | Scheiner et al. |
| 6,327,500 | B1 | 12/2001 | Cooper et al. |
| 6,330,477 | B1 * | 12/2001 | Casavant ........... A61N 1/3622 607/14 |
| 6,345,204 | B1 | 2/2002 | Scheiner et al. |
| 6,411,851 | B1 | 6/2002 | Winkler |
| 6,438,416 | B1 | 8/2002 | Michel |
| 6,438,418 | B1 | 8/2002 | Swerdlow et al. |
| 6,442,429 | B1 | 8/2002 | Hill et al. |
| 6,442,430 | B1 | 8/2002 | Ferek-Petric |
| 6,445,948 | B1 | 9/2002 | Somdahl et al. |
| 6,449,506 | B1 | 9/2002 | Sh. Revishvili et al. |
| 6,459,932 | B1 | 10/2002 | Mehra |
| 6,463,330 | B1 | 10/2002 | Rabinovitch et al. |
| 6,463,334 | B1 | 10/2002 | Flynn et al. |
| 6,470,211 | B1 * | 10/2002 | Ideker ............... A61N 1/3918 607/5 |
| 6,470,212 | B1 | 10/2002 | Weijand et al. |
| 6,477,420 | B1 | 11/2002 | Struble et al. |
| 6,477,422 | B1 | 11/2002 | Splett |
| 6,485,440 | B1 | 11/2002 | Gardeski |
| 6,487,443 | B2 | 11/2002 | Olson et al. |
| 6,501,983 | B1 | 12/2002 | Natarajan et al. |
| 6,501,994 | B1 | 12/2002 | Janke et al. |
| 6,505,082 | B1 | 1/2003 | Scheiner et al. |
| 6,510,342 | B1 | 1/2003 | Park et al. |
| 6,514,195 | B1 | 2/2003 | Ferek-Petric |
| 6,526,311 | B2 | 2/2003 | Begemann |
| 6,526,317 | B2 | 2/2003 | Hsu et al. |
| 6,539,257 | B1 | 3/2003 | KenKnight |
| 6,546,287 | B1 | 4/2003 | Havel et al. |
| 6,549,812 | B1 | 4/2003 | Smits |
| 6,556,862 | B2 | 4/2003 | Hsu et al. |
| 6,556,873 | B1 | 4/2003 | Smits |
| 6,560,484 | B1 | 5/2003 | Kroll et al. |
| 6,567,691 | B1 | 5/2003 | Stadler |
| 6,567,698 | B2 | 5/2003 | Herleikson |
| 6,574,505 | B1 | 6/2003 | Warren |
| 6,577,896 | B2 | 6/2003 | Werner et al. |
| 6,580,946 | B2 | 6/2003 | Struble |
| 6,587,720 | B2 | 7/2003 | Hsu et al. |
| 6,595,927 | B2 | 7/2003 | Pitts-Crick et al. |
| 6,609,028 | B2 | 8/2003 | Struble |
| 6,650,938 | B2 | 11/2003 | Boute |
| 6,650,941 | B2 | 11/2003 | Ferek-Petric |
| 6,654,637 | B2 | 11/2003 | Rouw et al. |
| 6,671,549 | B2 | 12/2003 | Van Dam et al. |
| 6,675,044 | B2 | 1/2004 | Chen |
| 6,695,790 | B2 | 2/2004 | Van Oort et al. |
| 6,711,442 | B1 | 3/2004 | Swerdlow et al. |
| 6,718,211 | B2 | 4/2004 | Smits |
| 6,721,597 | B1 | 4/2004 | Bardy et al. |
| 6,721,599 | B2 | 4/2004 | de Vries |
| 6,731,978 | B2 | 5/2004 | Olson et al. |
| 6,731,982 | B1 | 5/2004 | Kroll et al. |
| 6,741,893 | B2 | 5/2004 | Smits |
| 6,741,894 | B2 | 5/2004 | Michel |
| 6,745,073 | B1 | 6/2004 | Kroll |
| 6,745,076 | B2 | 6/2004 | Helland et al. |
| 6,745,081 | B1 | 6/2004 | Helland et al. |
| 6,748,270 | B2 | 6/2004 | Rouw et al. |
| 6,754,531 | B1 | 6/2004 | Kroll et al. |
| 6,760,615 | B2 | 7/2004 | Ferek-Petric |
| 6,763,266 | B1 | 7/2004 | Kroll |
| 6,766,196 | B1 | 7/2004 | Kroll et al. |
| 6,772,007 | B1 | 8/2004 | Kroll |
| 6,792,308 | B2 | 9/2004 | Corbucci |
| 6,795,731 | B1 | 9/2004 | Kroll et al. |
| 6,813,516 | B2 | 11/2004 | Ujhelyi et al. |
| 6,836,682 | B2 | 12/2004 | Van Dam |
| 6,847,842 | B1 | 1/2005 | Rodenhiser et al. |
| 6,873,870 | B2 | 3/2005 | Ferek-Petric |
| 6,882,882 | B2 | 4/2005 | Struble et al. |
| 6,889,078 | B2 | 5/2005 | Struble et al. |
| 6,901,291 | B2 | 5/2005 | Stoop et al. |
| 6,907,286 | B1 | 6/2005 | Kroll et al. |
| 6,910,084 | B2 | 6/2005 | Augustijn et al. |
| 6,915,169 | B2 | 7/2005 | Flynn et al. |
| 6,934,586 | B2 | 8/2005 | Struble et al. |
| 6,937,896 | B1 | 8/2005 | Kroll |
| 6,983,185 | B2 | 1/2006 | Ley et al. |
| 6,987,999 | B1 | 1/2006 | Kroll |
| 6,996,437 | B2 | 2/2006 | Kramm |
| 6,999,814 | B2 | 2/2006 | Hauser et al. |
| 7,006,867 | B1 | 2/2006 | Kroll |
| 7,020,517 | B2 | 3/2006 | Weiner |
| 7,024,244 | B2 | 4/2006 | Muhlenberg et al. |
| 7,027,861 | B2 | 4/2006 | Thompson |
| 7,027,862 | B2 | 4/2006 | Dahl et al. |
| 7,031,771 | B2 | 4/2006 | Brown et al. |
| 7,037,266 | B2 | 5/2006 | Ferek-Petric et al. |
| 7,047,071 | B2 | 5/2006 | Wagner et al. |
| 7,058,443 | B2 | 6/2006 | Struble |
| 7,058,450 | B2 | 6/2006 | Struble et al. |
| 7,076,290 | B2 | 7/2006 | Sheth et al. |
| 7,076,294 | B2 | 7/2006 | Bardy et al. |
| 7,076,298 | B2 | 7/2006 | Padmanabhan et al. |
| 7,079,891 | B1 | 7/2006 | Kroll |
| 7,082,336 | B2 | 7/2006 | Ransbury et al. |
| 7,096,063 | B2 | 8/2006 | Wanasek et al. |
| 7,103,409 | B2 | 9/2006 | Warren |
| 7,110,811 | B2 | 9/2006 | Wagner et al. |
| 7,113,822 | B1 | 9/2006 | Kroll |
| 7,120,490 | B2 | 10/2006 | Chen et al. |
| 7,120,496 | B2 | 10/2006 | Bardy et al. |
| 7,127,292 | B2 | 10/2006 | Warman et al. |
| 7,130,687 | B2 | 10/2006 | Cho et al. |
| 7,136,702 | B2 | 11/2006 | Wanasek |
| 7,139,611 | B1 * | 11/2006 | Kroll ................ A61N 1/368 607/28 |
| 7,142,927 | B2 | 11/2006 | Benser et al. |
| 7,142,928 | B2 | 11/2006 | Sharma et al. |
| 7,146,214 | B2 | 12/2006 | Struble |
| 7,149,577 | B2 | 12/2006 | Sharma et al. |
| 7,155,286 | B1 | 12/2006 | Kroll et al. |
| 7,162,300 | B2 | 1/2007 | van Groeningen et al. |
| 7,164,948 | B2 | 1/2007 | Struble et al. |
| 7,174,208 | B2 | 2/2007 | DeGroot et al. |
| 7,181,272 | B2 | 2/2007 | Struble et al. |
| 7,181,274 | B2 | 2/2007 | Rissmann et al. |
| 7,181,276 | B1 | 2/2007 | Province et al. |
| 7,190,245 | B2 | 3/2007 | Receveur et al. |
| 7,191,002 | B1 | 3/2007 | Kroll et al. |
| 7,194,304 | B1 | 3/2007 | Bornzin et al. |
| 7,200,438 | B2 | 4/2007 | Euler |
| 7,203,544 | B2 | 4/2007 | Legay et al. |
| 7,203,547 | B1 * | 4/2007 | Kroll ................ A61N 1/3622 607/34 |
| 7,215,998 | B2 | 5/2007 | Wesselink et al. |
| 7,231,249 | B2 | 6/2007 | Mower |
| 7,231,255 | B1 | 6/2007 | Kroll et al. |
| 7,233,822 | B2 | 6/2007 | Hettrick et al. |
| 7,239,925 | B2 | 7/2007 | Bardy et al. |
| 7,242,978 | B2 | 7/2007 | Cao et al. |
| 7,248,921 | B2 | 7/2007 | Palreddy et al. |
| 7,248,924 | B2 | 7/2007 | Casavant et al. |
| 7,274,962 | B2 | 9/2007 | Bardy et al. |
| RE39,897 | E | 10/2007 | Mower |

(56) References Cited

U.S. PATENT DOCUMENTS

| | | | |
|---|---|---|---|
| 7,277,745 B2 | 10/2007 | Natarajan et al. |
| 7,299,092 B2 | 11/2007 | Bardy et al. |
| 7,299,097 B2 | 11/2007 | Bardy et al. |
| 7,302,300 B2 | 11/2007 | Bardy et al. |
| 7,313,436 B2 | 11/2007 | Bardy et al. |
| 7,317,941 B2 | 1/2008 | Stomberg et al. |
| 7,330,757 B2 | 2/2008 | Ostroff et al. |
| 7,346,392 B2 | 3/2008 | KenKnight |
| 7,363,078 B2 | 4/2008 | Vonk et al. |
| 7,366,574 B2 | 4/2008 | Michel |
| 7,369,892 B2 | 5/2008 | Ferek-Petric |
| 7,376,458 B2 | 5/2008 | Palreddy et al. |
| 7,379,772 B2 | 5/2008 | Bardy et al. |
| 7,386,343 B1 | 6/2008 | Kroll et al. |
| 7,386,344 B2 | 6/2008 | Bocek et al. |
| 7,386,346 B2 | 6/2008 | Struble |
| 7,388,459 B2 | 6/2008 | Receveur et al. |
| 7,392,085 B2 | 6/2008 | Warren et al. |
| 7,392,095 B2 | 6/2008 | Flynn et al. |
| 7,428,437 B2 | 9/2008 | Bardy et al. |
| 7,444,182 B2 | 10/2008 | Ostroff et al. |
| 7,477,935 B2 | 1/2009 | Palreddy et al. |
| 7,480,351 B2 | 1/2009 | Hiatt, Jr. et al. |
| 7,496,408 B2 | 2/2009 | Ghanem et al. |
| 7,502,646 B2 | 3/2009 | Sheldon et al. |
| 7,502,647 B2 | 3/2009 | Sheldon et al. |
| 7,515,958 B2 | 4/2009 | Sheldon et al. |
| 7,515,959 B2 | 4/2009 | Hess |
| 7,522,958 B2 | 4/2009 | Ideker et al. |
| 7,522,959 B2 | 4/2009 | Hauser et al. |
| 7,529,589 B2 | 5/2009 | Williams et al. |
| 7,536,222 B2 | 5/2009 | Bardy et al. |
| 7,542,799 B2 | 6/2009 | Stoop et al. |
| 7,555,338 B2 | 6/2009 | Ostroff |
| 7,565,196 B2 | 7/2009 | Sheldon et al. |
| 7,577,480 B2 | 8/2009 | Zeijlemaker |
| 7,593,773 B2 | 9/2009 | Boute et al. |
| 7,596,410 B1 | 9/2009 | Kroll et al. |
| 7,599,740 B2 | 10/2009 | Betzold et al. |
| 7,617,007 B2 | 11/2009 | Williams et al. |
| 7,623,909 B2 | 11/2009 | Sanghera et al. |
| 7,623,913 B2 | 11/2009 | Phillips |
| 7,623,916 B2 | 11/2009 | Julian |
| 7,623,920 B2 | 11/2009 | Ostroff |
| 7,627,367 B2 | 12/2009 | Warran et al. |
| 7,627,375 B2 | 12/2009 | Bardy et al. |
| 7,634,316 B2 | 12/2009 | Swerdlow et al. |
| 7,643,877 B2 | 1/2010 | Dujmovic, Jr. et al. |
| 7,655,014 B2 | 2/2010 | Ko et al. |
| 7,657,311 B2 | 2/2010 | Bardy et al. |
| 7,986,992 B2 | 7/2011 | Ideker et al. |
| 8,175,702 B2 | 5/2012 | Efimov et al. |
| 8,473,051 B1 | 6/2013 | Wessels et al. |
| 8,560,066 B2 * | 10/2013 | Efimov | A61N 1/3956 607/5 |
| 8,706,216 B2 * | 4/2014 | Efimov | A61N 1/395 607/5 |
| 2002/0128565 A1 | 9/2002 | Rudy |
| 2003/0083727 A1 | 5/2003 | Casavant et al. |
| 2003/0220676 A1 | 11/2003 | Helland |
| 2004/0111123 A1 | 6/2004 | Ware et al. |
| 2004/0220641 A1 | 11/2004 | Wagner et al. |
| 2005/0096701 A1 | 5/2005 | Donovan et al. |
| 2005/0154420 A1 | 7/2005 | Diaz et al. |
| 2006/0161206 A1 * | 7/2006 | Efimov | A61B 5/0402 607/5 |
| 2007/0021793 A1 | 1/2007 | Voegele et al. |
| 2007/0088395 A1 | 4/2007 | Province et al. |
| 2009/0062877 A1 | 3/2009 | Krinski et al. |
| 2009/0204164 A1 * | 8/2009 | Efimov | A61N 1/3956 607/17 |
| 2010/0016917 A1 | 1/2010 | Efimov et al. |
| 2010/0324616 A1 | 12/2010 | Livnat et al. |
| 2011/0009916 A1 * | 1/2011 | Efimov | A61N 1/395 607/5 |
| 2011/0029032 A1 | 2/2011 | Bardy et al. |
| 2012/0203297 A1 | 8/2012 | Efimov et al. |
| 2013/0006319 A1 * | 1/2013 | Doerr | A61N 1/3624 607/4 |

FOREIGN PATENT DOCUMENTS

| | | |
|---|---|---|
| GB | 2 025 236 A | 1/1980 |
| WO | WO 1996/011035 A1 | 4/1996 |
| WO | WO 2006/042295 A1 | 4/2006 |
| WO | WO 2008/063498 A1 | 5/2008 |
| WO | WO 2009/108502 A1 | 9/2009 |
| WO | WO 2011/119662 A1 | 9/2011 |
| WO | WO 2011/146498 A2 | 11/2011 |
| WO | WO 2011/163339 A1 | 12/2011 |
| WO | WO 2012/012591 A2 | 1/2012 |
| WO | WO 2012/027252 A2 | 3/2012 |
| WO | WO 2013/102062 A1 | 7/2013 |

OTHER PUBLICATIONS

Niemann et al., "Intracardiac Voltage Gradients during Transthoracic Defibrillation: Implications for Postshock Myocardial Injury," Acad. Emerg. Med., Feb. 2005, 12(2):99-105, USA.

Kodama et al., "Aftereffects of high-intensity DC stimulation of the electromechanical performance of ventricular muscle", Am J. Physiol., 1994, 267:H248-H258, USA.

Li et al., "Defibrillation Shocks Produce Different Effects on Purkinje Fibers and Ventricular Muscle: Implications for Successful Defibrillation, Refibrillation and Postshock Arrhythmia", J Am Coll Cardiol, 1993, 22:607-614, USA.

Zhou et al., "Epicardial Mapping of Ventricular Defibrillation With Monophasic and Biphasic Shocks in Dogs," Circulation Research, Jan. 1993, 72(1):145-160, USA.

Li et al., "Mechanisms of enhanced shock-induced arrhythmogenesis in the rabbit heart with healed myocardial infarction," Am. J. Physiol. Heart Circ Physiol., May 3, 2005, 289:H1054-H1068, USA.

Sambelashvili et al., "Nonlinear effects in subthreshold virtual electrode polarization," Am. J. Physiol. Heart Circ, Physiol., 2003, 284(6):H2368-H2374, USA.

Aguel et al., "Advances in Modeling Cardiac Defibrillation," Int'l Journal of Bifurcation & Chaos, 2003, 13(12):3791-3803, USA.

Hillebrenner et al., "Postshock arrhythmogenesis in a slice of the canine heart," J. Cardiovasc. Electrophys., 2003, 14:S249-S256, USA.

Trayanova et al., "Virtual Electrode-Induced Positive and Negative Graded Responses: New Insights into Fibrillation Induction and Defibrillation," J. Cardiovascular Electrophysiology, 2003, 14(7):756-763, USA.

Larson et al., "Analysis of Electrically-Induced Reentrant Circuits in a Sheet of Myocardium," Annals Biomed. Eng., 2003, 31:768-780, USA.

Efimov, "Fibrillation or Neurillation: Back to the future in our concepts of sudden cardiac death?", Circ. Res., May 30, 2003, 92(10):1062-1064, USA.

Efimov et al., "Diastolic Shocking Experience: Do Virtual Anodes Exist Only During Systole?", J. Cardiovascular Electrophysiology, Nov. 2003, 14(11):1223-1224, USA.

Efimov et al., Fast Fluorescent Mapping of Electrical Activity in the Heart: Practical Guide to Experimental Design and Applications, Chapter 7, pp. 131-156, USA, 2003.

Cheng et al., "Shock-induced arrhythmogenesis is enhanced by 2,3-butanedione monoxime compared with cytochalasin D," Am. J. Physiol. Heart Circ. Physiol., 2004, 286:H310-H318, USA.

Takagi et al., "Unpinning and Removal of a Rotating Wave in Cardiac Muscle", Phys. Review Letters, Jul. 30, 2004, 93(5):058101-1-058101-4, USA.

Li et al., "Effects of Lidocaine on Shock-Induced Vulnerability", J. Cardiovascular Electrophysiology, Oct. 2003, 14(10):S237-S248, USA.

(56) References Cited

OTHER PUBLICATIONS

Cheng et al., "Mechanisms of Shock-Induced Arrhythmogenesis During Acute Global Ischemia", Am J Physiol. Heart Circ. Physiol., Jun. 2002, 282(6)H2141-51, USA.
Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577, USA.
Ashihara et al., "Spiral Wave Control by a Localized Stimulus: A Bidomain Model Study," J. Cardiovascular Electrophysiology, Feb. 2004 15(2):226-233, USA.
Ramanathan, "Noninvasive electrocardiographic imaging for cardiac electrophysiology and arrhythmia," Nature Medicine, Apr. 2004, 10(4):422-428, USA.
Nikolski et al., "Fluorescent Imaging of a Dual-Pathway Atrioventricular-Nodal Conduction System," Circ Res., Feb. 16, 2001, pp. 1-7, USA.
Qu et al., "The Gurvich waveform has lower defibrillation threshold than the rectilinear waveform and the truncated exponential waveform in the rabbit heart," Can. J. Physiol. Pharmacol., 2005, 83:152-160, USA.
Grosu et al., "Learning and Detecting Emergent Behavior in Networks of Cardiac Myocytes", Communications of the ACM, Mar. 2009, pp. 97-104, vol. 52, No. 3, USA.
Ripplinger et al., "Mechanisms of unpinning and termination of ventricular tachycardia", Am J. Physiol. Heart Circ. Physiol., 2006, pp. H184-H192, USA.
Sepulveda et al., "Current injection into a two-dimensional anisotropic bidomain", Biophys. J., vol. 55, May 1989, pp. 987-999, USA.
Allessie et al., "Regional Control of Atrial Fibrillation by Rapid Pacing in Conscious Dogs", Circulation, vol. 84, No. 4, Oct. 1991, pp. 1689-1697, USA.
Daoud et al., "Response of Type I Atrial Fibrillation to Atrial Pacing in Humans," Circulation, vol. 94, No. 5, 1996, 13 pages, USA.
Disertori et al., "Antitachycardia pacing therapies to terminate atrial tachyarrhythmias: the AT500 Italian Registry", European Heart Journal Supplements, 2001, pp. 16-24, USA.
Pumir et al., "Unpinning of a Rotating Wave in Cardiac Muscle by an Electric Field", J. Theor. Biol., vol. 199, 1999, pp. 311-319, USA.
Ladwig et al., "Absence of an Impact of Emotional Distress on the Perception of Intracardiac Shock Discharges," International Journal of Behavioral Medicine, 2003, 10(1):56-65, USA.
Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.
Efimov et al., "Virtual Electrode-Induced Phase Singularity: A Basic Mechanism of Defibrillation Failure," Circulation Research, 1998, 82(8):918-25, USA.
Efimov et al., "Transmembrane Voltage Changes Produced by Real and Virtual Electrodes During Monophasic Defibrillation Shock Delivered by an Implantable Electrode," Journal of Cardiovascular Electrophysiology, 1997, 8(9):1031-45, USA.
Cheng et al., "Virtual Electrode-Induced Reexcitation: A Mechanism of Defibrillation," Circulation Research, 1999, 85(11):1056-66, USA.
Fishler, "Syncytial Heterogeneity as a Mechanism Underlying Cardiac Far-Field Stimulation During Defibrillation-Level Shocks," Journal of Cardiovascular Electrophysiology, 1998, 9(4):384-94, USA.
Tsukerman et al., "Defibrillation of the Heart by a Rotating Current Field," Kardiologiia, 1973, 13(12):75-80, USA.
Zheng et al., "Reduction of the Internal Atrial Defibrillation Threshold with Balanced Orthogonal Sequential Shocks," Journal of Cardiovascular Electrophysiology, 2002; 13(9):904-9, USA.
Hucker et al., "Atrioventricular conduction with and without AV nodal delay: two pathways to the bundle of His in the rabbit heart", Am J. Physiol. Heart Circ. Physiol., 2007, 293:H1122-H1130, USA.
Mowrey et al., "Membrane Time Constant During Internal Defibrillation Strength Shocks in Intact Heart: Effects of Na+ and Ca2+ Channel Blockers," J. Cardiovascular Electrophysiology, Apr. 25, 2004, Jun. 8, 2008 and Jan. 2009, 20(1):85-92, USA.
Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.
Ideker et al., "Correlation Among Fibrillation, Defibrillation and Cardiac Pacing", Pacing Clin. Electrophysiol., vol. 18, Mar. 1995, pp. 512-525.
Sobie et al., "A Generalized Activating Function for Predicting Virtual Electrodes in Cardiac Tissue", Biophys. J., vol. 73, Sep. 1997, pp. 1410-1423.
Trayanova et al., "The Response of a Spherical Heart to a Uniform Electric Field: A Bidomain Analysis of Cardiac Stimulation", J. IEEE trans. Biomed. Eng., vol. 40, No. 9, Sep. 1993, pp. 899-908.
Davidenko et al., "Stationary and drifting spiral waves of excitation in isolated cardiac muscle," Nature, vol. 355, pp. 349-351, Jan. 23, 1992.
Gray et al., "Spatial and temporal organization during cardiac fibrillation," Nature, vol. 392, pp. 75-78, 1998.
Witkowski et al, "Spatiotemporal evolution of ventricular fibrillation," Nature, vol. 392, pp. 78-82, Mar. 5, 1998.
Cherry et al, "Visualization of spiral and scroll waves in simulated and experimental cardiac tissue", New J. Phys., vol. 10, 44 pp., 2008.
Koster et al., "A randomized trial comparing monophasic and biphasic waveform shocks for external cardioversion of atrial fibrillation," Am. Heart. J. vol. 147, pp. 828.e1-828.e7, 2004.
Babbs et al., "Therapeutic indices for transchest defibrillator shocks: Effective, damaging, and lethal electrical doses," Am. Heart J., vol. 99, No. 6, pp. 734-738, Jun. 1980.
Santini et al., "Single Shock Endocavitary Low Energy Intracardiac Cardioversion of Chronic Atrial Fibrillation," J. Interv. Card. Electrophysiol., vol. 3, pp. 45-51, 1999.
Sakurai et al., "Design and Control of Wave Propagation Patterns in Excitable Media," Science, vol. 296, pp. 2009-2012, Jun. 14, 2002.
Rappel et al, "Spatiotemporal Control of Wave Instabilities in Cardiac Tissue," Phys. Rev. Lett., vol. 83, No. 2, pp. 456-459, Jul. 12, 1999.
Fenton et al., "Multiple mechanisms of spiral wave breakup in a model of cardiac electrical activity," Chaos, vol. 12, No. 3, pp. 852-892, Sep. 2002.
Fenton et al., "Vortex dynamics in three-dimensional continuous myocardium with fiber rotation: Filament instability and fibrillation," Chaos, vol. 8, No. 1, pp. 20-47, Mar. 1998.
MacKenzie, "Making sense of a heart gone wild," Science, vol. 303, pp. 786-787, Feb. 6, 2004.
Walcott et al., "Do clinically relevant transthoracic defibrillation energies cause myocardial damage and dysfunction?" Resuscitation, vol. 59, pp. 59-70, 2003.
Plonsey, "The Nature of Sources of Bioelectric and Biomagnetic Fields," Biophys. J., vol. 39, pp. 309-312, 1982.
Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.
Sambelashvili et al., "Virtual electrode theory explains pacing threshold increase caused by cardiac tissue damage," Am. J. Physiol. Heart Circ. Physiol., vol. 286, pp. H2183-H2194, 2004.
Hooks et al, "Cardiac Microstructure: Implications for Electrical Propagation and Defibrillation in the Heart," Circ. Res., vol. 91, pp. 331-338, 2002.
Trayanova et al., "Modeling Defibrillation: Effects of Fiber Curvature," J. Electrocardiol., vol. 31 (suppl.), pp. 23-29, 1998.
Roth et al., "A Bidomain Model for the Extracellular Potential and Magnetic Field of Cardiac Tissue," IEEE Trans. Biomed. Eng., vol. 33, No. 4, pp. 467-469, Apr. 1986.
Murray, "The Physiological Principle of Minimum Work: I. The Vascular System and the Cost of Blood Volume," Proc. Natl. Acad. Sci. USA, vol. 12, pp. 207-214, 1926.
Kassab, "Scaling laws of vascular trees: of form and function," Am. J. Physiol. Heart Circ. Physiol., vol. 290, pp. H894-H903, 2006.

(56) References Cited

OTHER PUBLICATIONS

Maleckar et al., "Polarity reversal lowers activation time during diastolic field stimulation of the rabbit ventricles: insights into mechanisms," Am. J. Physiol. Heart Circ. Physiol., vol. 295, pp. H1626-H1633, 2008.
Kirchhof et al., "Regional entrainment of Atrial Fibrillation Studied by High-Resolution Mapping in Open-Chest Dogs," Circulation, vol. 88, pp. 736-749, 1993.
Pumir et al., "Wave Emission from Heterogeneities Opens a Way to Controlling Chaos in the Heart," Phys. Rev. Lett., vol. 99, pp. 208101-1-208101-4, 2007.
Gray et al, "Termination of spiral waves during cardiac fibrillation via shock-induced phase resetting," Proc. Natl. Acad. Sci. USA, vol. 102, No. 13, pp. 4672-4677, Mar. 29, 2005.
Gressard et al., "Pacing Lead/Myocardium Interface: Modeling and Characterization of the Impedance", Computers in Cardiology, vol. 32, pp. 901-903, 2005.
Klafter, "An Optimally Energized Cardiac Pacemaker," IEEE Trans Biomed. Eng., 1973, vol. 20, pp. 350-356.
Kostov et al., "Comparison Between Two Defibrillation Waveforms," Journal of Medical Engineering & Technology, Nov. 2010, vol. 34, Nos. 7-8, pp. 429-436.
Krasteva et al., "Transthoracic Defibrillation with Chopping-Modulated Biphasic Waveforms," Journal of Medical Engineering & Technology, vol. 25, No. 4, Jul./Aug. 2001, pp. 163-168.
Antropov et al., "An Experimental Defibrillator with Programmable Pulse Shape," Biomedical Engineering, vol. 41, No. 1, Nov. 2007, pp. 7-11.
Sweeney et al., "Defibrillation Using a High-Frequency Series of Monophasic Rectangular Pulses: Observations and Model Predictions," J. Cardiovasc Electrophysiology, 1996, vol. 7, pp. 134-143.
Janardhan et al., "Multi-Stage Electrotherapy Delivered Through Chronically Implanted Leads Terminates Atrial Fibrillation with Lower Energy than a Single Biphasic Shock," Journal of the American College of Cardiology, 2013, 27 pages.
Walcott et al., "Internal Atrial Cardioversion with Ultrashort Pulses," Heart Rhythm 2012—33rd Annual Scientific Sessions, May 2012, 1 page.
Janardhan et al., "A Novel Low-Energy Electrotherapy that Terminates Ventricular Tachycardia with Lower Energy than a Biphasic Shock when Antitachycardia Pacing Fails," Journal of the American College of Cardiology, 2012, vol. xx, No. x, 6 pages.
Wenwen et al., "Low-Energy Multistage Atrial Defibrillation Therapy Terminates Atrial Fibrillation with Less Energy than a Single Shock," Circ. Arrhythm Electrophysiol, 2011, pp. 917-925.
Gerstenfeld et al, "Internal Atrial Defibrillation Revisited—How low can we go?," Journal of the American College of Cardiology, 2013, 9 pages.
Winkle, "Evolution of the Implantable Cardioverter-Defibrillator," Journal of the American College of Cardiology, 2012, vol. xx, No. x, 3 pages.
Luther et al., "Low-Energy Control of Electrical Turbulence in the Heart," Macmillan Publishers Limited, Jul. 2011, vol. 475, pp. 235-241.
Berger et al., "Instead of Defibrillator's Painful Jolt, There May be a Gentler Way to Prevent Suddent Death, According to Hopkins Scientists," Press Release Johns Hopkins Medicine, 2011, 1 page.
Supplementary Partial European Search Report for European Application No. 08858734.0, dated Nov. 17, 2011, 11 pages.
European Patent Office, European Office Action for European Application No. 05825356.8, dated Oct. 5, 2009, 6 pages, Munich, Germany.
Written Opinion/Search Report for Int'l Application No. PCT/US2008/086483, dated Jun. 25, 2009, 14 pages.
Search Report for Int'l Application No. PCT/US2012/072046, dated Apr. 25, 2013, 3 pages.
Application and File history for U.S. Appl. No. 13/340,637, filed Dec. 19, 2011, now U.S. Pat. No. 8,473,051. Inventors: Shelton et al.
Fenton et al., "Termination of Atrial Fibrillation Using Pulsed Low-Energy Far-Field Stimulation," Circulation, vol. 120, pp. 467-476, 2009.
PCT/US2012/072046, International Search Report, dated Apr. 25, 2013, 3 pages.
PCT/US2005/040187, Written Opinion, dated Feb. 24, 2009, 6 pages.
PCT/US2007/023836, International Search Report, dated Apr. 9, 2008, 7 pages.
PCT/US2008/086483, International Search Report, dated Jun. 25, 2009, 14 pages.
PCT/US2011/033547, International Search Report, dated Jan. 17, 2012, 4 pages.
PCT/US2008/086483, Written Opinion, dated Jun. 15, 2010, 7 pages.
Terry, Medtronic Model 7250 Jewel AF Implantable Cardioverter Defibrillator System, Dec. 5, 2000, 15 pages.
Gold et al., Clinical Experience with a Dual-Chamber Implantable Cardioverter Defibrillator to Treat Atrial Tachyarrhythmias, Nov. 2001, 7 pages.
Wellens et al., Atrioverter: An Implantable Device for the Treatment of Atrial Fibrillation, 1998, 7 pages.
Daoud et al., Initial Clinical Experience with Ambulatory Use of an Implantable Atrial Defibrillator for Conversion of Atrial Fibrillation, 2000, 8 pages.
Cooper et al., Internal Cardioversion of Atrial Fibrillation, 1997, 9 pages.
Lok et al., Clinical Shock Tolerability and Effect of Different Right Atrial Electrode Locations on Efficacy of Low Energy Human Transvenous Atrial Defibrillation Using an Implantable Lead System, Nov. 1, 1997, 7 pages.

* cited by examiner

D0 ACD D2
TO
RA + 1 RA + 2
ANY COMBINATION OF ELECTRODE
COILS TO ANY COMBINATION OF
ELECTRODE COILS PRE
IMPLANT AND AMBULATORY

MULTI-STAGE ATRIAL CARDIOVERSION THERAPY LEADS

RELATED APPLICATION

The present application claims the benefit of U.S. Provisional Patent Application No. 61/674,145, filed Jul. 20, 2012, titled "Multi-Stage Atrial Cardioversion Therapy Leads," the disclosure of which is hereby incorporated by reference.

TECHNICAL FIELD

The present invention is generally directed to devices, systems and methods for treating atrial fibrillation. More specifically, the present invention is directed to implantable electrical leads for delivering multi-stage, atrial cardioversion therapy to a patient.

BACKGROUND

Traditional electrical shock therapies for treating an atrial arrhythmia in a patient typically include delivery of a series of mono- or biphasic shocks, each shock, or pulse, often having a similar electrical characteristic. To deliver such traditional therapy, a wide variety of electrical leads may be used. However, for multi-stage electrical shock therapies, each stage having a potentially different electrical characteristic, the use of standard, known leads may be insufficient.

BRIEF DESCRIPTION OF THE DRAWINGS

The invention may be more completely understood in consideration of the following detailed description of various embodiments of the invention in connection with the accompanying drawings, in which.

Figure 1:
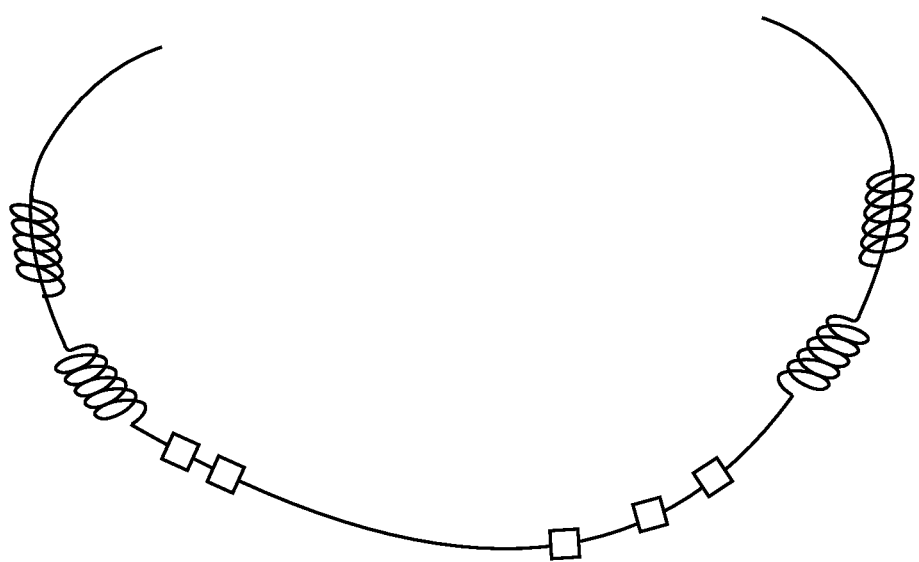
FIG. 1 depicts an embodiment of a single-pass multi-stage therapy lead, according to an embodiment of the claimed invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

When applying multi-stage therapies, there exists a clinical need to minimize lead hardware and maximize therapy options. Embodiments of the present invention minimize the total number of leads required, thereby increasing ease and speed of an implant, and may reduce the total number of conductors in leads, thereby increasing reliability. Published U.S. Patent Application No. 2012/0209343 to Efimov et al., describes and depicts a number of multi-stage atrial cardioversion therapies, the contents of which, other than the claims and express teachings, are herein incorporated by reference in their entirety. Further, it will be understood that the details and variations of construction of leads in accordance with the various embodiments of the present invention can be accomplished in any number of manners of lead construction known to a person of skill in the art and/or in accordance with conventional or proposed standards for implantable leads such as the International Standard 1 (IS-1), DF-1, and IS-6 standards, the disclosures and details of such standards being incorporated herein by reference.

Embodiments of the claimed invention include one or more electrical leads as described below and as depicted in FIGS. 1-9. Embodiments of the claimed leads may incorporate one or more of the concepts and or features described below. Each concept may be included in existing leads and/or combined into a multi-stage therapy (MST) lead, which is a lead specifically designed to reduce complexity and time of implant and maximize therapeutic options for delivery of bi-atrial multi-stage therapy (or simply bi-atrial and/or one or more stage therapy).

In an embodiment, the claimed invention comprises a lead having an electrode configuration having physiologic spacing that permits maximum physiologic response.

Referring to FIG. 1, the lead comprises a plurality of high-voltage coils in the coronary sinus and right atrial superior vera cava. The distance between coils permits or facilitate a single-pass lead. So, these distal coronary sinus coils are a physiologic specific distance, (given other dual or multi-coil lead configurations) between each other. The clinical objective is to maximize the trans-atrial electrical field for any therapy, but also for multi-stage therapy.

In an embodiment, the lead comprises a plurality of pacing electrodes proximal to the MST coil (vs. tip-ring being distal to the coil) both in the left atrial CS to permit bi-atrial or uni-bi-atrial pacing.

In another embodiment, the lead includes a plurality of electrodes in the right atrium (i.e, not in the coronary sinus) and will permit pacing or sensing of electrical activity.

The spacing of the LA (non-descending) coronary sinus electrodes and coils are unique to human physiology to permit the reduction of the number of the total number of leads.

In an embodiment, the lead includes a coil length which is matched to the physiologic need to maximally cover the left atrium without creating a shortened pathway to the right atrial coils. The lead may accommodate a physiologic distance to one or more physiologically positioned coils so as to maximize atrial recruitment.

Figure 2:
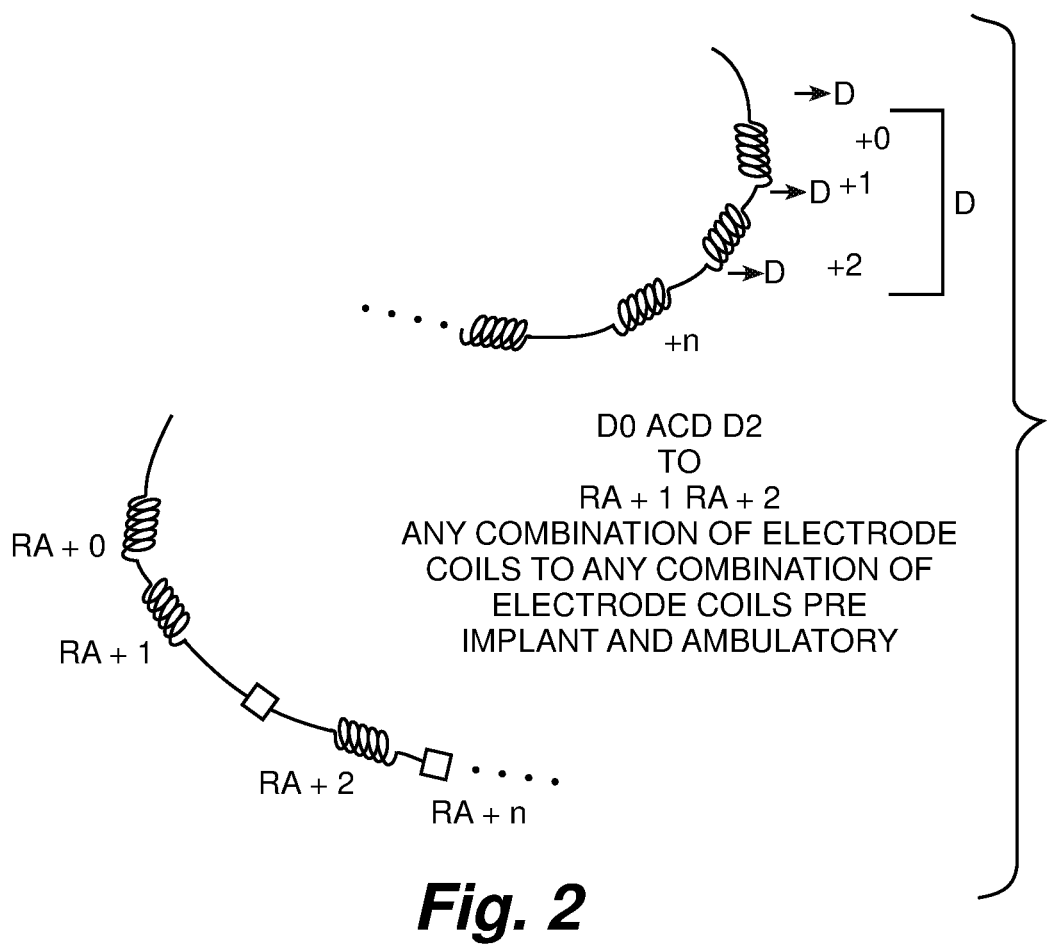
FIG. 2 depicts a switchable and selectable lead, according to an embodiment of the claimed invention.

Referring to FIG. 2, in another embodiment, the lead includes switchable/selectable coil pairs and/or more coils. Embodiments of the claimed invention may be combined with methods and apparatuses for switching and selecting as known by those skilled in the art, such that any combination of electrode coils or any combination of electrode coils, pre-implant and ambulatory, are possible.

Such embodiments of the claimed invention may include the ability to select electrode coil pairs pre-implant, per implant or ambulatory for the purpose to maximize first, second, third, or even nth stage therapy. Some such therapies may be coil-delivered, not pacing-delivered, Rx.

Figure 3:
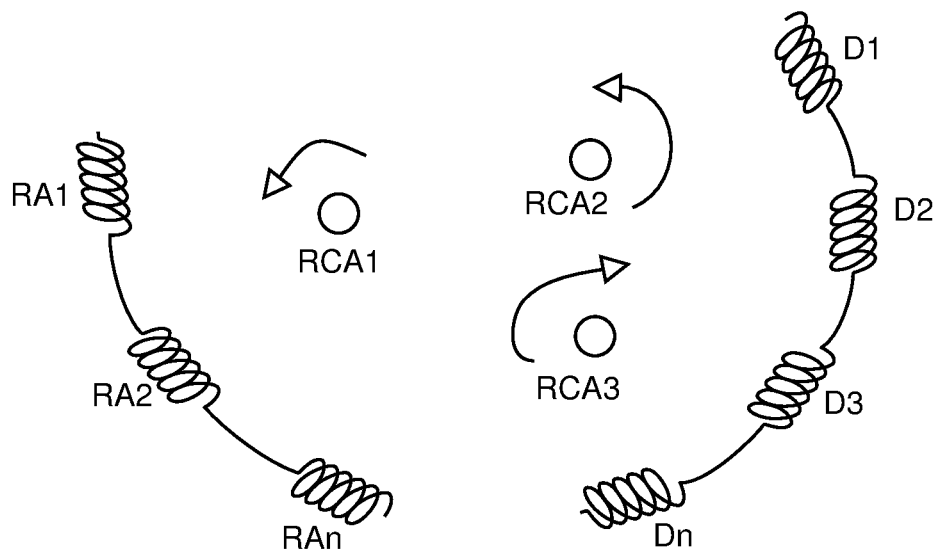
FIGS. 3-6 depict embodiments of leads of the claimed invention as applied to treat an atrial arrhythmia.

Referring also to FIG. 3, the ability to select electrode coil pairs pre-implant or ambulatory may facilitate the maximization of one or more of a first, second, third, or nth stage therapy/Rx. Such therapies may be coil-delivered or pacing-delivered therapies.

Defibrillatory efficacy or refractory extension prolongation while minimizing required energy: Stage 1, 2, . . . n therapy may be delivered for arranging disruption (unpinning) and refractory period. Prolongation is phase dependent and, thus, position of energy dependent. As depicted in FIG. 3, re-entrant circuit arrhythmia 1, 2 and 3 may be operating in a unique and asynchronous or synchronous fashion (i.e., RCA1 may or may not support RCA2 or RCA3). To maximize the effect of disruption/unpinning and/or refractory period modification: Therapy may be delivered to maximize current density between two or more coils. So, D3 to RA1 may impact RCA3 and RCA1, which may be dominate foci and thus disrupt RCA2's ability to sustain—do not need to reach RCA1, 2 and 3—just the dominate foci at that time for that arrhythmia. Alternatively, if RCA3 was dominate, RAn to D3 may address RCA3, not reaching RCA1 or RCA2 with energy, but that was not needed, as the lower energy RCA3 pair effectively disrupted the interrelationship to RCA1 and RCA2 indirectly terminating entire arrhythmia.

Figure 4:
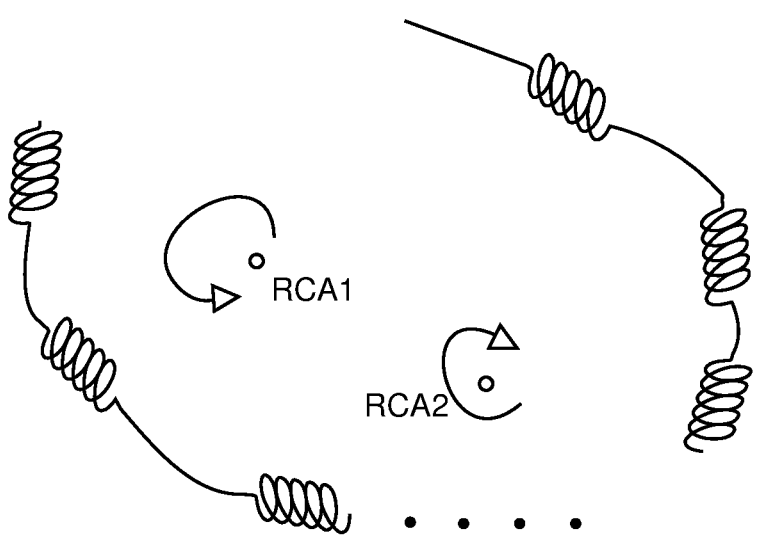
Figure 5:
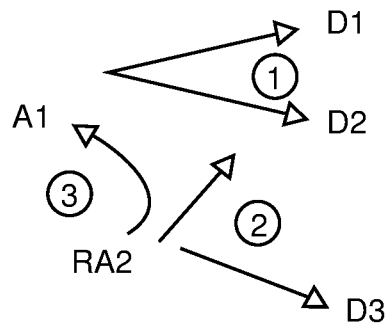

Referring also to FIGS. 4 and 5, in an embodiment, the claimed invention is adapted and configured to find/disrupt the arrhythmia. The system of leads may search to deliver therapy through any number of combinations of coils. The system may search through numerous coil pairs/combination to seek out the presenting arrhythmia because time is not life critical. So, while a total of 1 Joule between any two pair may reliably disrupt an arrhythmia, one would search $C_m^n$ combinations of, say, 0.1 J therapies between any number of coil combinations, for example, therapy (1) is between RA1 and D1/D2.

Embodiments of the claimed invention may include a series of these combinations of therapies which first disrupt and then extinguish the arrhythmia. For example, the therapy may require delivery of first combination pathway (2) followed by (3) and then (1) to be successful. The arrhythmia becomes unpinned at, for example, RCA2 only to become established around RCA1, whereby sequence (3) then (2), terminate the arrhythmia.

In an embodiment, the system learns which combination works best to establish which arrhythmia. The sequence of therapies which maximizes termination with minimal energy becomes probabilistically the therapy delivered and/or attempted. The system watches to determine which therapies and therapy combination are most effective.

Figure 6:
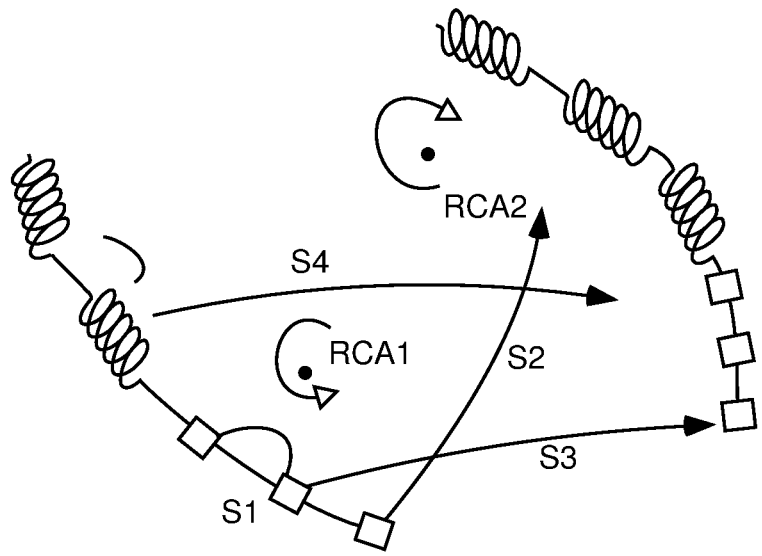

Referring to FIG. 6, in an embodiment, the system monitors the arrhythmia on any number of combinations of coils and electrodes. Given that any arrhythmia is subject to measurement observation—RCA1 will appear different when obscured on S1, S4, etc.

Figure 7:
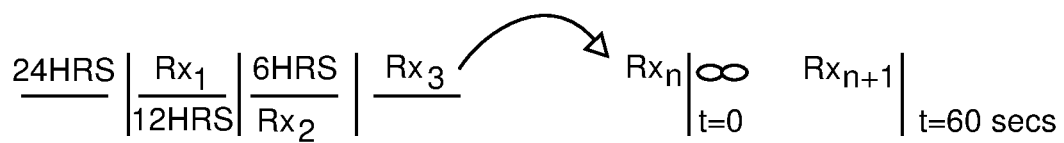
FIG. 7 depicts the selection of leads and lead combinations depending on arrhythmia maturity.

Referring also to FIG. 7, the treatment of arrhythmias may be dependent not only on the combination of stage therapy, the pair or number of poles (coils and/or electrode combinations) but the maturity of the arrhythmia.

For an arrhythmia of longer duration, a more aggressive therapy ($Rx_1$) may be required. As noted above, the therapy may be comprised of any number of stages and/or combinations of therapy stages delivered through any number of combinations of coils/electrodes. Given that shorter duration arrhythmias are more easily terminated, the therapy may start with less aggressive and, presumably, less perceptible therapy.

Figure 8:
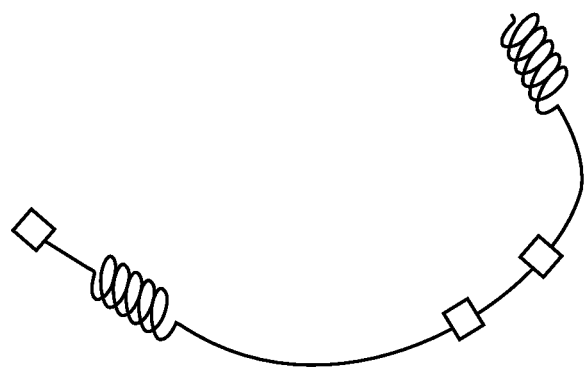
FIG. 8 depicts another lead, according to an embodiment of the claimed invention.

Referring to FIG. 8, a number of pacing electrodes proximal to the distal coil located at a physiologic distance from the coils and electrodes which would permit physiologic B12-atrial pacing from a single-pass MST B1-atrial pacing lead, the electrodes would be selectable. As described elsewhere for 1 to n electrodes, these would be selected to maximize therapy and minimize current drain. The electrodes could be coils.

Any number of selectable electrode configurations have been previously disclosed herein. Here the use of passive electrical devices leverage the relative energy delivered between various coils, electrodes given the relative energy levels of Stage 1 and on. The concept is to minimize the number of unique conductors relative to the current pathways.

Figure 9:
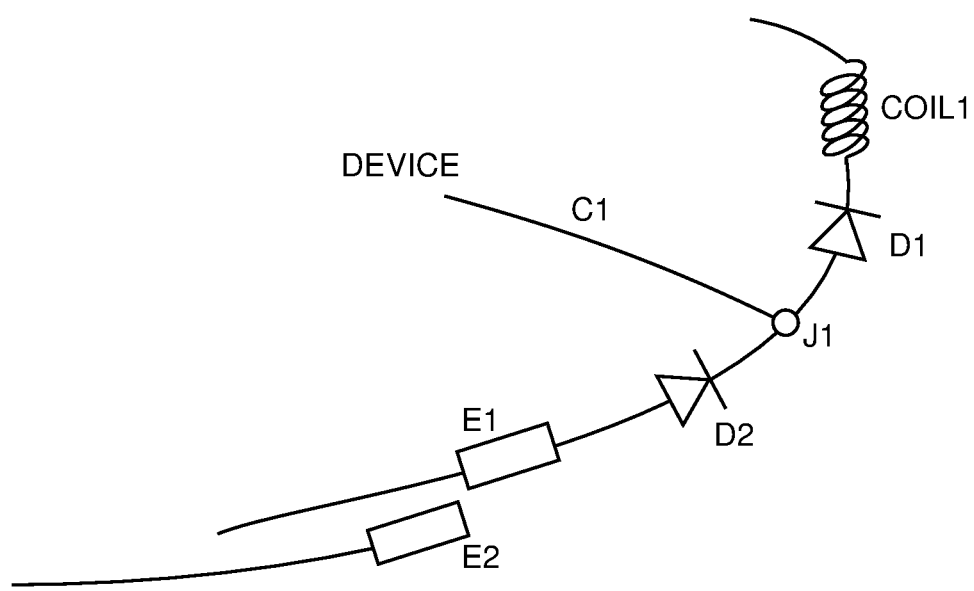
FIG. 9 depicts yet another lead, according to an embodiment of the claimed invention.

Referring also to FIG. 9, the selective use of passive diodes can be used to direct current. For example, fewer conductors can be used knowing different energy will be delivered down differing electrode/coil configurations.

So, in an embodiment, to deliver S1 therapy, conductor C1 is energized through junction J1. Diode D1 is forward biased and diode D2 is reverse biased, preventing current from flooding to electrode E1. The S1 therapy is channeled to coil 1. If pacing therapy is, for example, delivered to E1 with C1 being the return pathway (V=0), current is preferentially directed back to the device through C1. Diode 1 offset voltage say 0.7 v, is not overcome and little/no current flows to coil 1.

Various embodiments of the claimed invention are further described and depicted in the attached document Attachment A, "Multi-Stage Therapy Leads", comprising 6 pages. Attachment A is incorporated by reference herein in its entirety.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

In one example embodiment, an implantable apparatus is provided for treatment of atrial arrhythmia of a patient using an implantable therapy generator. The apparatus includes: a single-pass lead configured for implantation in the patient such that no electrodes are within a right ventricle of a heart of the patient, the lead including: a proximal portion configured to be connectable to the implantable therapy generator; a body portion having at least two electrodes, the lead configured such that when implanted in the patient the at least two electrodes on the body portion are positioned within or adjacent a right atrium of a heart of a patient; and a distal portion having at least two electrodes, the lead configured such that when implanted in the patient the at least two electrodes on the distal portion are positioned within a blood vessel proximate the left atrium, wherein the implantable therapy generator is programmed to deliver a multi-stage therapy by activating various combinations of at least one electrode of the body portion of the lead and at least one electrode of the distal portion of the lead in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia.

In another example embodiment, a method includes: providing a single-pass lead configured for implantation in a patient, the lead including: a proximal portion configured to be connectable to the implantable therapy generator; a body portion having at least two electrodes; and a distal portion having at least two electrodes; and providing instructions, the instructions comprising: implanting the single-pass lead in the patient such that the at least two electrodes on the body portion are positioned within or adjacent a right atrium of a heart of a patient, and such that the at least two electrodes on the distal portion are positioned within a blood vessel proximate the left atrium, and further such that no electrodes are within a right ventricle of a heart of the patient; and causing the implantable therapy generator to deliver a multi-stage therapy according to a program, wherein various combinations of at least one electrode of the body portion of the lead and at least one electrode of the distal portion of the lead are activated in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia, wherein each of the stages includes a plurality of pulses.

In an additional example embodiment, a method is provided for treating atrial arrhythmias in a patient with a single-pass lead, the lead including a proximal portion configured to be connectable to the implantable therapy generator, a body portion having at least two electrodes, and a distal portion having at least two electrodes. The method includes: implanting the single-pass lead in the patient such that the at least two electrodes on the body portion are positioned within or adjacent a right atrium of a heart of a patient, and such that the at least two electrodes on the distal portion are positioned within a blood vessel proximate the left atrium, and further such that no electrodes are within a right ventricle of a heart of the patient; and causing the implantable therapy generator to deliver a multi-stage therapy according to a program, wherein various combinations of at least one electrode of the body portion of the lead and at least one electrode of the distal portion of the lead are activated in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia, wherein each of the stages includes a plurality of pulses.

The invention claimed is:

1. An implantable apparatus for treatment of atrial arrhythmia of a patient using an implantable therapy generator, the apparatus comprising:
   a single-pass lead configured for implantation in the patient such that no electrodes are within a right ventricle of a heart of the patient, the lead including:
      a proximal portion configured to be connectable to the implantable therapy generator;
      a body portion having at least two electrodes, the lead configured such that when implanted in the patient the at least two electrodes on the body portion are positioned within or adjacent a right atrium of a heart of a patient; and
      a distal portion having at least two electrodes, the lead configured such that when implanted in the patient the at least two electrodes on the distal portion are positioned within a blood vessel proximate a left atrium,
   wherein the implantable therapy generator is programmed to deliver a multi-stage therapy by activating various combinations of at least one electrode of the body portion of the lead and at least one electrode of the distal portion of the lead in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia, wherein each of the stages includes a plurality of pulses, and
   wherein the single pass lead is oriented such that the proximal portion, the body portion, and the distal portion at least partially surround the right atrium and the left atrium of the heart.

2. The apparatus of claim 1, wherein the body portion of the lead includes at least one ring electrode and at least one coil electrode, and wherein the distal portion of the lead includes at least one ring electrode and at least one coil electrode.

3. The apparatus of claim 2, wherein the various combinations of electrodes are selectable prior to, during, or after implant of the apparatus.

4. The apparatus of claim 1, wherein in response to detection of a location of a reentrant cardiac arrhythmia, the implantable therapy generator is further programmed to deliver a multi-stage therapy by activating at least two pairs of electrodes, wherein each pair of electrodes includes at least one electrode on the body portion of the lead and at least one electrode on the distal portion of the lead.

5. The apparatus of claim 1, wherein each stage of the multi-stage therapy includes a duration, and wherein each therapy stage duration is dependent upon a duration of the atrial arrhythmia.

6. The apparatus of claim 1, wherein each stage of the multi-stage therapy includes a duration, and wherein the duration of each successive therapy stage is longer than the duration of the previous stage.

7. The apparatus of claim 1, wherein the implantable therapy generator is further programmed to deliver an additional therapy subsequent to the multi-stage therapy, the additional therapy programmed to activate one electrode on the distal portion of the lead to provide cardiac pacing.

8. A method, comprising:
providing a single-pass lead configured for implantation in a patient, the lead including:
a proximal portion configured to be connectable to the implantable therapy generator;
a body portion having at least two electrodes; and
a distal portion having at least two electrodes; and
providing instructions, the instructions comprising:
implanting the single-pass lead in the patient such that the at least two electrodes on the body portion are positioned within or adjacent a right atrium of a heart of a patient, and such that the at least two electrodes on the distal portion are positioned within a blood vessel proximate a left atrium, and further such that no electrodes are within a right ventricle of a heart of the patient, wherein the single pass lead is oriented such that the proximal portion, the body portion, and the distal portion at least partially surround the right atrium and the left atrium of the heart; and
causing the implantable therapy generator to deliver a multi-stage therapy according to a program, wherein various combinations of at least one electrode of the body portion of the lead and at least one electrode of the distal portion of the lead are activated in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia, wherein each of the stages includes a plurality of pulses.

9. The method of claim 8, wherein the body portion of the lead includes at least one ring electrode and at least one coil electrode, and wherein the distal portion of the lead includes at least one ring electrode and at least one coil electrode.

10. The method of claim 9, further comprising selecting the various combinations of electrodes are prior to, during, or after implant of the apparatus.

11. The method of claim 8, the instructions further comprising:
causing the implantable therapy generator to deliver a multi-stage therapy in response to detection of a location of a reentrant cardiac arrhythmia, the therapy to activate at least two pairs of electrodes, wherein each pair of electrodes includes at least one electrode on the body portion of the lead and at least one electrode on the distal portion of the lead.

12. The method of claim 8, wherein each stage of the multi-stage therapy includes a duration, and wherein each therapy stage duration is dependent upon a duration of the atrial arrhythmia.

13. The method of claim 8, wherein stage of the multi-stage therapy includes a duration, and wherein the duration of each successive therapy stage is longer than the duration of the previous stage.

14. The method of claim 8, further comprising delivering an additional therapy subsequent to the multi-stage therapy, the additional therapy programmed to activate one electrode on the distal portion of the lead to provide cardiac pacing.

15. A method of treating atrial arrhythmias in a patient with a single-pass lead, the lead including a proximal portion configured to be connectable to the implantable therapy generator, a body portion having at least two electrodes, and a distal portion having at least two electrodes, the method comprising:
implanting the single-pass lead in the patient such that the at least two electrodes on the body portion are positioned within or adjacent a right atrium of a heart of a patient, such that the at least two electrodes on the distal portion are positioned within a blood vessel proximate a left atrium, further such that no electrodes are within a right ventricle of a heart of the patient, and wherein the single pass lead is oriented such that the proximal portion, the body portion, and the distal portion at least partially surround the right atrium and the left atrium of the heart; and
causing the implantable therapy generator to deliver a multi-stage therapy according to a program, wherein various combinations of at least one electrode of the body portion of the lead and at least one electrode of the distal portion of the lead are activated in response to an indication an atrial arrhythmia has occurred, the multi-stage therapy including at least a first stage for unpinning of one or more singularities associated with the atrial arrhythmia, a second stage for anti-repinning of the one or more singularities associated with the atrial arrhythmia, and a third stage for extinguishing of the one or more singularities associated with the atrial arrhythmia, wherein each of the stages includes a plurality of pulses.

16. The method of claim 15, further comprising:
causing the implantable therapy generator to deliver a multi-stage therapy in response to detection of a location of a reentrant cardiac arrhythmia, the therapy to activate at least two pairs of electrodes, wherein each pair of electrodes includes at least one electrode on the body portion of the lead and at least one electrode on the distal portion of the lead.

17. The method of claim 15, wherein each stage of the multi-stage therapy includes a duration, and wherein each therapy stage duration is dependent upon a duration of the atrial arrhythmia.

18. The method of claim 15, wherein each stage of the multi-stage therapy includes a duration, and wherein the duration of each successive therapy stage is longer than the duration of the previous stage.

19. The method of claim 15, wherein the body portion of the lead includes at least one ring electrode and at least one coil electrode, and wherein the distal portion of the lead includes at least one ring electrode and at least one coil electrode.

20. The method of claim 15, further comprising delivering an additional therapy subsequent to the multi-stage therapy, the additional therapy programmed to activate one electrode on the distal portion of the lead to provide cardiac pacing.

* * * * *